(12) United States Patent
Herrmann et al.

(10) Patent No.: US 12,318,146 B2
(45) Date of Patent: Jun. 3, 2025

(54) TECHNIQUE FOR DETERMINING A POSITION OF ONE OR MORE IMAGED MARKERS IN AN IMAGE COORDINATE SYSTEM

(71) Applicant: Stryker European Operations Limited, Carrigtwohill (IE)

(72) Inventors: Florian Herrmann, Schwanau (DE); Hans Schoepp, Freiburg (DE)

(73) Assignee: Stryker European Operations Limited, Carrigtwohill (IE)

( * ) Notice: Subject to any disclaimer, the term of this patent is extended or adjusted under 35 U.S.C. 154(b) by 171 days.

(21) Appl. No.: 17/229,314

(22) Filed: Apr. 13, 2021

(65) Prior Publication Data
US 2021/0322104 A1    Oct. 21, 2021

(30) Foreign Application Priority Data
Apr. 15, 2020    (EP) .................................... 20169620

(51) Int. Cl.
*A61B 34/20*    (2016.01)
*A61B 34/10*    (2016.01)
*G06T 7/00*    (2017.01)

(52) U.S. Cl.
CPC .............. *A61B 34/20* (2016.02); *A61B 34/10* (2016.02); *G06T 7/0012* (2013.01);
(Continued)

(58) Field of Classification Search
CPC ...... A61B 2034/107; A61B 2034/2068; A61B 34/10; A61B 34/20; A61B 6/12;
(Continued)

(56) References Cited

U.S. PATENT DOCUMENTS 6,484,049 B1    11/2002    Seeley et al.
7,570,987 B2     8/2009    Raabe et al.
(Continued)

FOREIGN PATENT DOCUMENTS

DE    4417414 A1    12/1994
EP    3326564 A1     5/2018
WO    2019012520 A1  1/2019

OTHER PUBLICATIONS

English language abstract and machine-assisted English translation for DE 44 17 414 A1 extracted from espacenet.com database on Apr. 15, 2021, 7 pages.

*Primary Examiner* — Keith M Raymond
*Assistant Examiner* — Milton Truong
(74) *Attorney, Agent, or Firm* — Howard & Howard Attorneys PLLC (57) ABSTRACT

A method and a device for determining a respective position of one or more markers in a 3D image coordinate system are provided. A plurality of image data sets taken from a 3D volume in which an object and one or more markers are disposed. The 3D volume comprises a central volume containing at least a portion of the object and further comprises a peripheral volume adjacent to the central volume and containing the one or more markers. The image data sets have been taken from at least one of different positions and different orientations relative to the object. A first subset comprises image data sets that each includes at least one dedicated marker of the one or more markers and a second subset comprises at least one image data set that does not include the at least one dedicated marker. The method further comprises determining, from the image data sets, a position of the at least one dedicated marker in a 3D image coordinate system of a 3D reconstruction of the central volume with the object portion.

20 Claims, 7 Drawing Sheets

(52) U.S. Cl.
CPC . *A61B 2034/107* (2016.02); *A61B 2034/2068* (2016.02); *G06T 2207/10081* (2013.01); *G06T 2207/10116* (2013.01)

(58) Field of Classification Search
CPC ...... A61B 2090/367; A61B 2090/3983; A61B 2090/36; G06T 2207/10081; G06T 2207/10116; G06T 7/0012
See application file for complete search history.

(56) References Cited

U.S. PATENT DOCUMENTS

| | | | |
|---|---|---|---|
| 8,483,434 B2 | 7/2013 | Buehner et al. | |
| 2003/0059097 A1* | 3/2003 | Abovitz | A61B 6/12 382/294 |
| 2003/0130576 A1 | 7/2003 | Seeley et al. | |
| 2006/0050848 A1 | 3/2006 | Vilsmeier et al. | |
| 2007/0253541 A1* | 11/2007 | Sukovic | A61B 90/36 378/205 |
| 2012/0201421 A1* | 8/2012 | Hartmann | A61B 6/5235 382/103 |
| 2013/0006120 A1* | 1/2013 | Druse | A61B 90/39 600/476 |
| 2013/0066196 A1* | 3/2013 | Graumann | A61B 6/547 600/424 |
| 2018/0150960 A1* | 5/2018 | Derda | G06T 7/0012 |
| 2018/0185113 A1* | 7/2018 | Gregerson | A61B 34/35 |

* cited by examiner

TECHNIQUE FOR DETERMINING A POSITION OF ONE OR MORE IMAGED MARKERS IN AN IMAGE COORDINATE SYSTEM

PRIORITY CLAIM

This application claims priority under 35 U.S.C. § 119 to European Patent Application No. 20169620.0, filed Apr. 15, 2020, the entire contents of which are hereby incorporated by reference.

TECHNICAL FIELD

The present disclosure generally relates to a technique for determining a position of one or more imaged markers in a three-dimensional (3D) image coordinate system. The technique may in particular be implemented in a medical scenario, for example in the context of surgical navigation.

BACKGROUND

One way to digitally reconstruct a three dimensional volume is to capture a plurality of images from different positions or orientations of said three dimensional volume. Based on the plurality of images, a 3D reconstruction can be generated that contains information about the location of various imaged features inside the three dimensional volume. Such 3D reconstructions are generated, for example, in material science or in medical imaging such as computer tomography (CT) or radiography using a C-arm.

The plurality of images is often captured using X-ray beams due to their high transmittance for most materials. Particularly in case of medical imaging, the plurality of images are focused onto a small central volume containing only body parts essential to the surgical procedure in order to reduce potential harmful radiation exposure to the patient caused by the X-ray beams. The 3D reconstruction is consequently limited to the central volume.

The 3D reconstruction thus obtained sometimes has to be registered relative to a 3D navigation coordinate system that is used for surgical navigation. In such a navigation context, it is common to use markers for registration purposes. However, the markers on, within or in the vicinity of the patient's body may not be arranged close enough to be comprised in the central volume (e.g., due to a distance between an organ of interest and a patient surface supporting the markers) and therefore are not represented in the 3D reconstruction, see, for example, U.S. Pat. No. 7,570,987 B2.

One approach to obtain the marker positions in the 3D reconstruction would be to increase the size of the central volume so that the markers are located inside the central volume. Such techniques, which locate the markers within an imaged central volume such that the markers are visible in each image taken, are disclosed in US 2003/0130576 A1 and EP 3 326 564 A1. A schematic representation of such techniques is shown in FIG. 1B, wherein between an X-ray sensor 14 and an X-ray source 16 of a C-arm rotatable around an axis 22 a central volume 24 is defined that includes an arrangement of multiple markers 30. However, when taking images of a central volume 24 enlarged so as to also include the markers 30, the volume of the patient's body exposed to radiation would increase also, which increases the undesired aforementioned health risk.

While, therefore, the markers 30 should be located outside the central volume 24 to decrease a patient's exposure to radiation, it would nonetheless be desirable to obtain information about the position of the markers 30 relative to reconstructed central volume 24 in a 3D image coordinate system.

SUMMARY

There is a need for a technique that solves one or more of the aforementioned or other problems.

According to one aspect, a computer-implemented method of determining a respective position of one or more markers in a 3D image coordinate system is provided. The computer-implemented method comprises obtaining a plurality of image data sets taken from a 3D volume in which an object and one or more markers are disposed. The 3D volume comprises a central volume containing at least a portion of the object and further comprises a peripheral volume adjacent to the central volume and containing the one or more markers. The image data sets have been taken from at least one of different positions and different orientations relative to the object. A first subset comprises image data sets that each includes at least one dedicated marker of the one or more markers and a second subset comprises at least one image data set that does not include the at least one dedicated marker. The computer-implemented method further comprises determining, from the image data sets, a position of the at least one dedicated marker in a 3D image coordinate system of a 3D reconstruction of the central volume containing the object portion.

The computer-implemented method may comprise selecting, from the image data sets, at least two image data sets of the first subset. In this variant, the position of the at least one dedicated marker in the 3D image coordinate system of the 3D reconstruction of the central volume containing the object portion is determined from the selected image data sets.

The at least one dedicated marker may be included in a portion of the peripheral volume that is not included in the at least one image data set of the second subset. As such, one or more or all of the markers may generally be included (e.g., imaged) in less then all of the image data sets taken form the 3D volume.

The central volume may be covered entirely in all image data sets. The peripheral volume may be covered less than entirely in at least some of the image data sets. Therefore, a 3D reconstruction of the peripheral volume may be less accurate than a 3D reconstruction of the central volume. This means that the marker position(s) will be less accurate also, but still usable for the envisaged (e.g., registration) purpose.

The image data sets may have been generated using projection-based imaging technique. The image data sets may be representative of projections of the 3D volume on an imaging line or imaging plane. Optionally, the central volume may be covered entirely by the projections and the peripheral volume may be covered less than entirely by the projections.

The projections of the 3D volume may be captured from radiation that was transmitted through the object. The radiation may be X-rays. The image data sets may be generated using a C-arm and/or CT imaging techniques.

The computer-implemented method may further comprise visualizing the 3D reconstruction of the central volume, for example in the context of surgical navigation. The peripheral volume may be excluded from visualization.

The computer-implemented method may further comprise processing the position of the at least one dedicated marker for surgical navigation. For example, the at least one dedicated marker may be associated with a known position in a 3D navigation coordinate system, and processing the position of the at least one dedicated marker for surgical navigation may comprise registering the 3D image coordinate system with the 3D navigation coordinate system.

The one or more markers may be one or more artefacts of one or more devices trackable by a surgical navigation system. Optionally, the one or more trackable devices may be or may comprise one or more light emitting diodes (LEDs) each having a solder joint constituting the associated artefact (i.e., the associated marker). In other variants, the one or more trackable devices may be or may comprise one or more passive elements (e.g., capable of reflecting radiation such as light for navigation or other purposes) that also generate artefacts in the image data sets. The artefacts may generally have a fixed and predefined positional relationship relative to the trackable devices (or their LEDs or passive elements). Alternatively, or in addition, the one or more trackable devices may be or may comprise one or more coils each configured to detect electromagnetic radiation and to constitute the artefact.

The object portion may be an interior portion of the object. The object may be a patient or a body part of the patient, such as an organ, bone, parts of the nervous system, or a portion thereof.

The one or more markers may be loosely arranged relative to the object. For example, the one or more markers may be provided on a registration device comprising, in addition to the one or more markers as reference markings for a surgical imaging device, a tracker (with, e.g., one or more LEDs or reflective elements) capable of being tracked by a camera of a navigation system. The one or more markers may have a known spatial relationship relative to the tracker. An exemplary registration device in this regard is described in U.S. Pat. No. 8,483,434 B2, herein incorporated by reference.

Alternatively, the one or more markers may be attached to the object, in particular to an exterior portion thereof. In case the object is a patient or a body part of the patient, the exterior portion of the patient may be a skin surface.

The one or more markers may comprise two or more markers arranged together on a carrier. Optionally, at least a first portion of the carrier may be flexible such that a first one of the markers on the first portion is movable relative to a second one of the markers on the first portion. At least a second portion of the carrier may be rigid such that a first one of the markers on the second portion is rigidly held in position relative to a second one of the markers on the second portion. The carrier may be attached to the object (e.g., the skin surface of a patient) by an adhesive.

The central volume may have a substantially cylindrical shape. The cylindrical shape of the central volume may define a longitudinal axis. Each of the image data sets may be centred relative to the longitudinal axis (e.g., a projection of the longitudinal axis on an image plane symmetrically may cut the image plane in two halves). The cylindrical shape may define a diameter perpendicular to its longitudinal axis. When a projection-based imaging technique is used, that diameter may correspond an opening dimension of a projection on the imaging plane or imaging line in a vicinity of the longitudinal axis.

Independent of its shape, the central volume may have a longitudinal axis. The image data sets may have been taken by one of (i) moving an imaging device to different positions about or along the longitudinal axis of the central volume and (ii) moving the object and the one or more markers about or along the longitudinal axis.

The imaging device for generating the image data sets may operate on the basis of radiation, such as X-rays. The image data sets may have been generated by one of computer tomography and an X-ray device coupled to a C-arm.

According to a second aspect a computer program product is provided, wherein the computer program product comprises program code portions configured to perform the computer-implemented method described herein when executed by a processor. The computer program product may be stored on a computer-readable recording medium. The computer-readable recording medium may be a non-transitory recording medium.

According to a third aspect, a device for determining a respective position of one or more markers in a 3D image coordinate system is provided. The device is configured to obtain a plurality of image data sets taken from a 3D volume in which an object and the one or more markers are disposed. The 3D volume comprises a central volume containing at least a portion of the object and further comprises a peripheral volume adjacent to the central volume and containing the one or more markers. The image data sets have been taken from at least one of different positions and different orientations. A first subset comprises image data sets that each includes at least one dedicated marker of the one or more markers and a second subset comprises at least one image data set that does not include the at least one dedicated marker. The device is configured to determine, from the image data sets, a position of the at least one dedicated marker in a 3D image coordinate system of a 3D reconstruction of the central volume containing the object portion.

The device may be configured to select, from the image data sets, at least two image data sets of the first subset. In this variant, the position of the at least one dedicated marker in the 3D image coordinate system of the 3D reconstruction of the central volume containing the object portion is determined from the selected image data sets.

The device may be configured to perform any of the computer-implemented methods and computer-implemented method aspects described herein.

According to a fourth aspect, a navigation system is provided, wherein the navigation system comprises the device of the third aspect as described herein and a processing device configured to process the position of the at least one dedicated marker for navigation. The navigation system may be a surgical navigation system. The navigation system may be configured to track one or more devices, such as passive or active tracking elements, using a camera system. The camera system may comprise a stereo camera.

BRIEF DESCRIPTION OF THE DRAWINGS

Further details, advantages and aspects of the present disclosure will become apparent from the following embodiments taken in conjunction with the drawings, wherein.

DETAILED DESCRIPTION

In the following description, exemplary embodiments of a technique for determining a respective position of one or more markers in a 3D image coordinate system will be explained with reference to the drawings. The same reference numerals will be used to denote the same or similar structural features. It will be appreciated that the technique can be embodied in a method, a device, a system, a computer program product, or otherwise.

The technique described herein comprises obtaining a plurality of image data sets. For an easier understanding of how the image data sets are obtained, an exemplary process of capturing these image data sets is described first. While the technique can be used in medical and non-medical fields, such as material science, it will in the following be explained with reference to medical imaging.

Two common projection-based medical imaging technologies are computer tomography (CT) and X-ray imaging using a C-arm. In both technologies, image data sets of an object are taken from different orientations and/or positions relative to the imaged object. CT usually uses an imaging line, i.e., projections onto a substantially one dimensional sensor, whereas X-ray imaging using a C-arm typically uses an imaging plane, i.e., projections onto a two dimensional sensor. The technique herein is not limited to X-ray imaging and may be used with any other radiation.

Figure 1A:
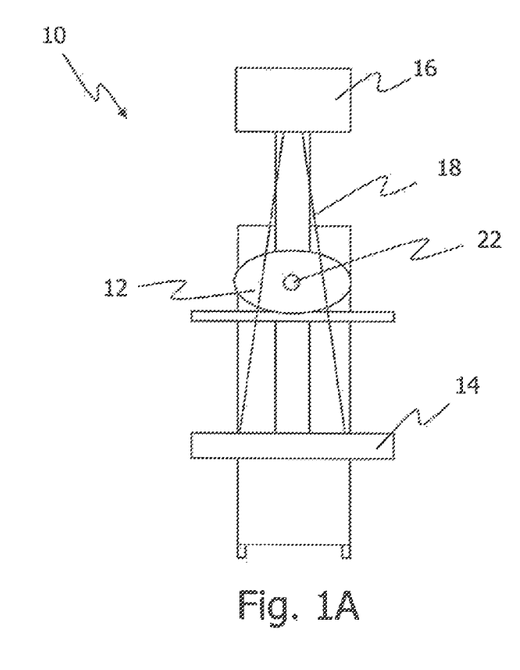
FIG. 1A shows a C-arm configured to capture image data sets of an object.
Figure 1B:
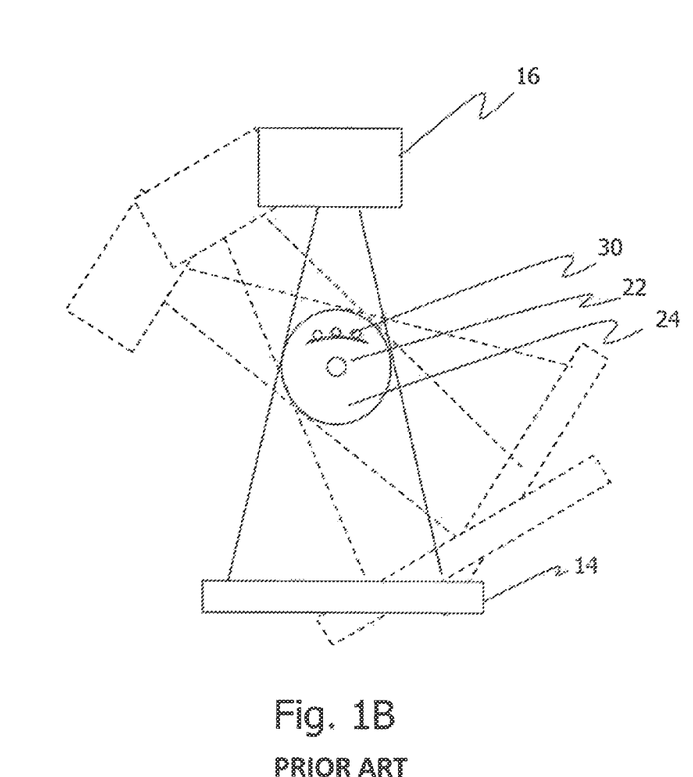
FIG. 1B shows a C-arm in three different tilting angles according to a prior art approach.

FIG. 1A shows an exemplary C-arm 10 configured to capture image data sets of an object 12 to be imaged in accordance with certain embodiments of the present disclosure. The object 12 may be any biological or non-biological specimen. The object 12 may, for example, be a patient or a body part of a patient.

The C-arm 10 shown in FIG. 1A comprises an imaging device in form of an X-ray sensor 14 and an X-ray source 16, which both are movable simultaneously in rotatory motion around a longitudinal axis 22. The object 12 is arranged to be intersected by (e.g., co-linear with) the longitudinal axis 22 and is therefore located between the X-ray sensor 14 and the X-ray source 16. Due to its rotatory movability, the C-arm 10 shown in FIG. 1A is capable of capturing image data sets of the object 12 from different positions and different orientations. Alternatively, an imaging device may be provided that is configured to capture image data sets only from different positions (e.g., using an X-ray sensor and an X-ray detector that both move in a straight path) or only from different orientations (e.g., using a pivoting X-ray sensor or X-ray source).

In the process of capturing image data so as to obtain an image data set, X-rays are emitted from the X-ray source 16 that reach the X-ray sensor 14 after passing through the object 12. A portion of the X-rays is absorbed or scattered by the object 12. The resulting image data captured by the X-ray sensor 14 is indicative of a spatial distribution of differently absorbing matter in the object 12 and therefore of a projection of a volume between the X-ray source 16 and the X-ray sensor 14 onto an imaging plane, wherein the image plane is a sensor area of the X-ray sensor 14. Due to the finite sensor area of the X-ray sensor 14, the X-rays that reach the X-ray sensor 14 are confined to a probing X-ray beam 18 that covers a limited solid angle (e.g., in a cone-like manner).

An image data set may consist of or comprise the image data generated by a capturing process from a given position and/or orientation. In some variants, an image data set may additionally comprise information about the position and/or orientation underlying the associated image data capturing process.

The C-arm 10 shown in FIG. 1A is configured to generate a plurality of image data sets from different angles by rotating the X-ray source 16 together with the X-ray sensor 14 around the object 12.

FIG. 1B shows an abstract representation of the C-arm 10 in three different tilting angles around the longitudinal axis 22 relative to a set of markers 30. In this example, which reflects the prior art cited in the introductory portion of this description, the markers 30 are contained in every image taken since the markers are located in a central volume 24 imaged in each rotational position of the C-arm 10.

Figure 1C:
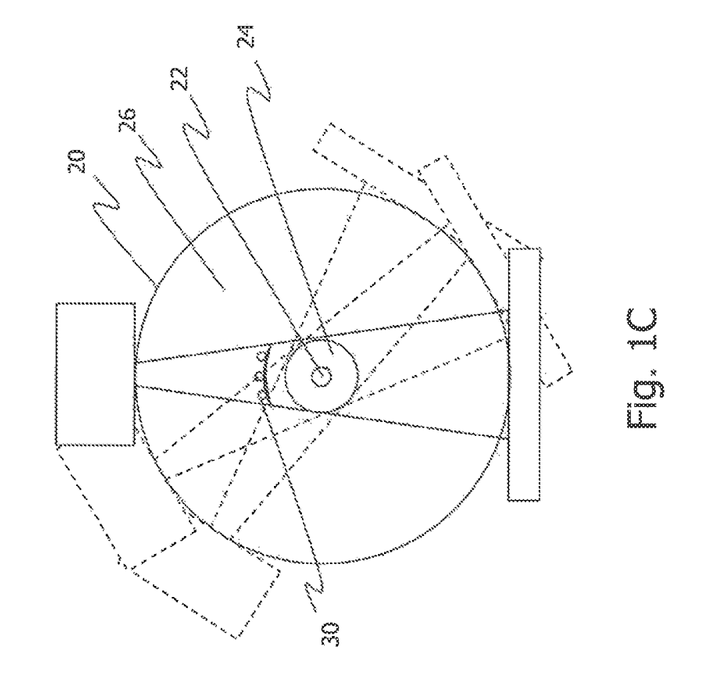
FIG. 1C shows a C-arm in three different tilting angles according to an embodiment.

FIG. 1C illustrates an embodiment in which the central volume 24 has been chosen smaller compared to the illustration in FIG. 1B, so that the markers 30 will only be contained in a subset of the images taken by the C-arm 10.

In more detail, FIG. 1C shows an abstract representation of three different tilting angles of the C-arm 10 around the longitudinal axis 22 relative to the object 12. In practice, the tilting angle is usually changed in smaller increments as shown in FIG. 1C. The C-arm may rotate in angular increments such as 1°, 2°, 3° or more before capturing the next image data set. Over the course of capturing the plurality of image data sets, the C-arm 10 may move for a full rotation of 360°, a fraction thereof (e.g., 180°) or more than one rotation (e.g., 540°). For example, the C-arm 10 may move for a full rotation of 360° with 3.6° increments for each image data set. In such a case, the C-arm 10 captures 100 image data sets.

It is not required that an imaging device 10 moves relative to the object 12 in order to capture the image data sets. Alternatively, the object 12 may be moved relative to the imaging device 10. Such movement may comprise moving the object 12 about or along a longitudinal axis, such as the longitudinal axis 22 shown in FIG. 1A that is arranged between the X-ray sensor 14 and the X-ray source 16.

Any volume that can be covered by the imaging device 10 may be defined as a 3D volume 20. In the case shown in FIG. 1C, the exemplary C-arm 10 moves around the entire angular range of 360° so that the 3D volume 20 essentially describes a cylindrical shape arranged coaxially with the longitudinal axis 22 of the C-arm 10. The radius of the 3D volume 20 reaches up to the X-ray sensor 14 and X-ray source 16. In the case of FIGS. 1A and 1C, the X-ray sensor 14 and X-ray source 16 are spaced in an equal distance away from the longitudinal axis 22. In the case of different distances, the 3D volume 20 reaches up to the component with the larger distance relative to the longitudinal axis 22.

As can be seen in FIG. 1C, the 3D volume 20 comprises in its centre around the longitudinal axis 22 a central volume 24. The central volume 24 is covered by probing X-ray beams 18 (and the associated projections on the X-ray sensor 14) for any tilting angle of the C-arm 10. The central volume 24 can therefore be defined as a volumetric intersection of all probing X-ray beams 18 (and the associated projections). Consequently, any feature arranged in the central volume 24 is included in all of the captured image data sets.

The 3D volume 20 further comprises a peripheral volume 26 adjacent to the central volume 24. In FIG. 1C the peripheral volume 26 is located radially adjacent relative to the central volume 24 and therefore essentially describes the shape of a hollow cylinder. The central volume 24 and the peripheral volume 26 may have other shapes, which may depend, for example, on the paths of the X-ray sensor 14 and the X-ray source 16, the covered angular range, and the size of the angular increments. Features located in the peripheral volume 26, such as the markers 30, are not necessarily covered by all probing X-ray beams 18. Therefore, such features may not be included in all of the captured image data sets.

It should be noted that defining the central volume 24 as the volumetric intersection of all probing X-ray beam 18 is one of many ways to define the central volume 24. Alternatively, the central volume 24 may be smaller or larger than the volumetric intersection of all probing X-ray beams 18. The size of the central volume 24 will be discussed further below in the context of a 3D reconstruction that is based on the central volume 24.

The C-arm 10 comprises or is connected to at least one processor and at least one storage medium (not shown). The X-ray sensor 14 is configured to generate the image data sets based on X-rays received at the X-ray sensor 14. The processor is configured to receive the image data sets from the X-ray sensor 14 and store the image data sets on the storage medium.

Based on the image data sets, the processor is configured to generate a 3D reconstruction of at least a part of the 3D volume. The 3D reconstruction may be performed by a method known in prior art. The 3D reconstruction is arranged in a 3D image coordinate system and may, for example, be represented in form of voxels or a point cloud.

The 3D reconstruction recreates features that are included in the image data sets taken by the C-arm 10. Evidently, accuracy of the 3D reconstruction of a feature improves with the number of image data sets that include said feature. As explained above, features that are located in the central volume 24 shown in FIGS. 1A and 1C are included in every image data set. On the other hand, features that are arranged in the peripheral volume 26 are not included in all image data sets. Therefore, a 3D reconstruction of features inside the central volume 24 has a higher accuracy than 3D reconstruction of features inside the peripheral volume 26.

Since accuracy of a 3D reconstruction of the peripheral volume 26 is comparably lower, 3D reconstruction is conventionally only performed for the central volume 24. This means the output of a C-arm or a similar imaging system is, or permits, a 3D reconstruction of the central volume 24 only, whereas any information regarding the peripheral volume is typically discarded.

In the example of FIG. 1C, the central volume 24 is defined as a volumetric intersection of all probing X-ray beams 18, which is essentially the largest portion of the 3D volume 20 that is covered by every X-ray projection (i.e., every probing X-ray beam 18). Alternatively, a smaller portion of the volumetric intersection may be selected as central volume 24. A 3D reconstruction based on such a volume contains less data and requires less computing resources. Further alternatively, a portion of the 3D volume 20 that is larger than the volumetric intersection may be selected as the central volume 24.

Figure 2A:
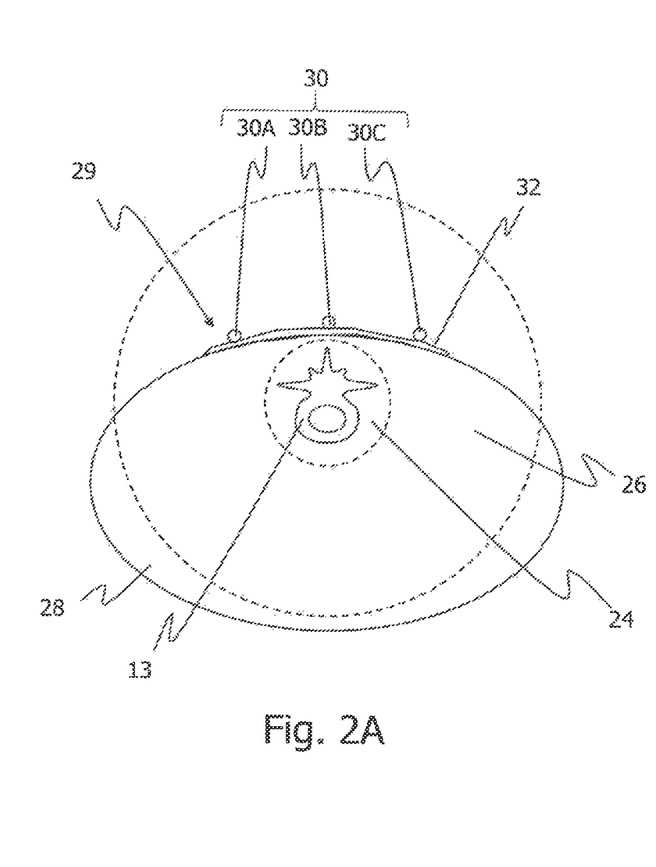
FIG. 2A shows a cross-section of a patient within a 3D volume with a schematic illustration of an associated central volume and peripheral volume.

FIG. 2A shows a cross section of a patient 28 to be imaged. Also illustrated in FIG. 2A are a central volume 24 and a peripheral volume 26. These volumes 24, 26 are defined as explained above with reference to FIGS. 1A and 1C.

The central volume 24 is focused onto an object within the patient's body of interest for surgical navigation. The object may be the patient's spine. In the example shown in FIG. 2A, the central volume 24 is focused on an object in form of one or more vertebrae 13. Therefore, 3D reconstruction will be performed for the central volume 24 containing the vertebra 13. The 3D reconstruction could also be performed for the central volume 24 and at least a part of the peripheral volume 26. Further, the central volume 24 may alternatively cover any other body part of the patient, such as an organ, a bone, or skin tissue.

For the purpose of surgical navigation, the 3D reconstruction needs to be registered with a 3D navigation coordinate system of a surgical navigation system. Such registration is based on markers that can be imaged by the C-arm 10 or other imaging device (i.e., that are detectable in the image data sets). As the markers are arranged on, in or in the vicinity of the object 12 to be imaged, the plurality of image data sets are captured (e.g., pre- or intra-operatively) by the imaging device such as the C-arm 10 as described with reference to FIGS. 1A and 1C above. During surgical navigation, the markers are still arranged at, in or in vicinity of the object 12. Consequently, the markers themselves or tracking elements having a fixed and predefined spatial relationship relative to an associated marker can be identified by the surgical navigation system (e.g., by a camera thereof) and assigned to coordinates in the 3D navigation coordinate system. Based on a determination of positions of the markers in a 3D image coordinate system (i.e., relative to the 3D reconstruction of the central volume 24) and a determination of associated positions of the markers (or the associated tracking elements) in the 3D navigation coordinate system, the 3D reconstruction can be registered relative to the 3D navigation coordinate system by aligning the marker coordinates in the 3D image coordinate system with the marker (or tracking element) coordinates in the 3D navigation coordinate system (optionally taking into account the relative position between each marker and its associated tracking element).

Having thus explained utilization of markers for exemplary registration purposes in a surgical navigation context, FIG. 2A further shows a trackable device 29 comprising a flexible carrier 32 that supports a plurality of such markers 30 (e.g., three markers 30A, 30B, and 30C), wherein the carrier 32 is attached via an adhesive to a skin surface on the back of the patient 28. The carrier 32 shown in FIG. 2A is flexible and therefore adapts to any movement of the patient's skin, wherein the markers 30 may be movable relative to each other. A large number of markers 30 may be located on a frame like flexible carrier 32 having a central opening through which surgery is performed, such as the SpineMask™ tracker distributed by Stryker Navigation. The SpineMask™ tracker may thus be considered an example of the trackable device 29.

Optionally, the carrier 32 may at least partially be rigid. In such a case the markers may be rigidly located relative to each other. In further embodiments, the trackable device 29 may comprise an interface for attaching the carrier 32 to the patient 28. The interface may comprise at least one of a clamp, a screw, and a magnet.

The markers 30 shown in FIG. 2A are defined by LEDs on the carrier 32 and, more precisely, by the solder joints of these LEDs. The solder joints are easily detectable as artefacts in the image data sets as they substantially block any X-rays from reaching the X-ray sensor 14 (see FIGS. 1A and 1C). The LEDs on the carrier 32, in turn are easily detectable by a camera of a surgical navigation system. As such, the surgical navigation system may determine the positions of the LEDs in a 3D navigation coordinate system, and the positions of the associated solder joints may be determined in a 3D image coordinate system. Based on a predetermined spatial relationship between the solder joints and the associated LEDs (e.g., a predetermined spatial vector including the null vector), the 3D image coordinate system can thus be registered relative to the 3D navigation coordinate system.

In still further embodiments, the markers may be provided on a carrier that is configured to be loosely arranged relative (e.g., besides) the patient 28. See, for example, the registration device of U.S. Pat. No. 8,483,434 B2, that could also be used in embodiments of the present disclosure. The registration device comprises, in addition to the one or more markers, tracking elements (such as LEDs) capable of being tracked by a camera of a navigation system, wherein the markers may have a known spatial relationship relative to the tracking elements.

As illustrated in FIG. 2A, the central volume 24 is focused onto the vertebrae 13 inside the patient 28. As such, the central volume 24 does not cover the markers 30, or at least not all of them. Therefore, any 3D reconstruction of the central volume 24 with the vertebrae 13 will likewise not contain the markers 30 (or at least not all of them). Consequently, the 3D reconstruction of the central volume 24 alone cannot be used for registration purposes in the context of surgical navigation.

Figure 2B:
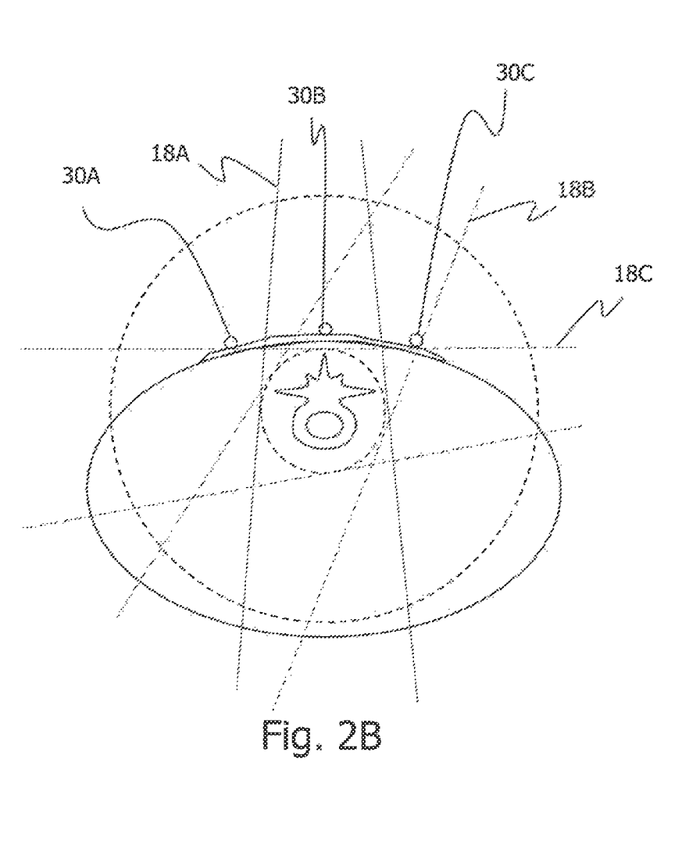
FIG. 2B shows examples of projecting X-ray beams through the 3D volume.

FIG. 2B shows examples of probing X-ray beams 18 projected through the 3D volume 20, wherein some beams 18 do and some do not cover markers 30. For example, probing X-ray beams 18A and 18B cover marker 30B, but probing X-ray beam 18C does not cover marker 30B. More specifically, probing X-ray beam 18A covers marker 30B. Probing X-ray beam 18B covers markers 30B and 30C. And probing X-ray beam 18C does not cover any of markers 30A, 30B, or 30C.

Figure 3:
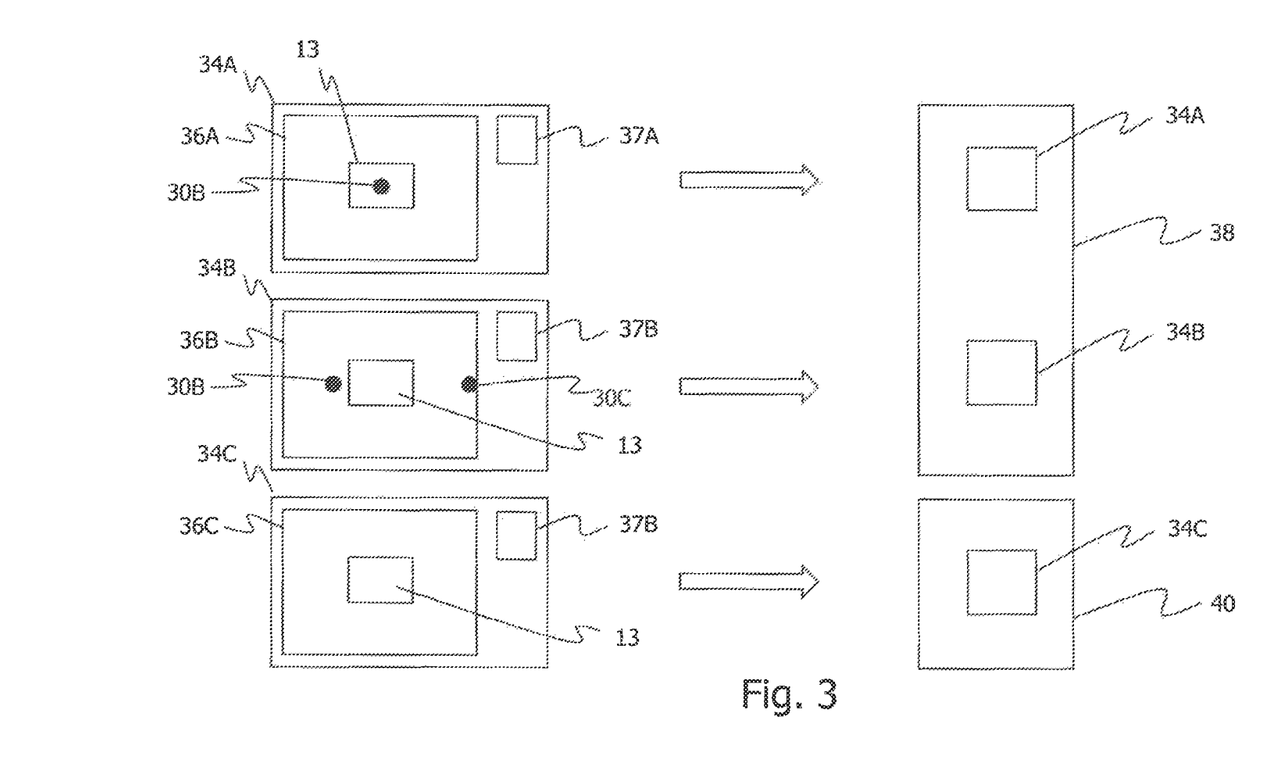
FIG. 3 shows image data sets resulting from different X-ray beam projections.

FIG. 3 shows image data sets 34 generated as projections resulting from the different X-ray beams 18A, 18B, 18C. Image data set 34A comprises image data 36A captured using X-ray beam 18A. Image data set 34B comprises image data 36B captured using X-ray beam 18B and image data set 34C comprises image data 36C captured using X-ray beam 18C. Optionally, each of the image data sets 34 may comprise additional parameters 37A, 37B, 37C, respectively, such as the tilting angle of the C-arm 10 (as will be described further below).

The following explanations exemplarily focus on one dedicated marker, namely marker 30B. However, these explanations may be applied to any other marker 30 and any combination of markers 30.

With continued reference to FIG. 3, two subsets 38, 40 of image data sets can be defined. A first subset 38 comprises all of the captured image data sets 34 that each include the dedicated marker 30B (i.e., image data sets 34A and 34B with image data 36A and 36B captured using the probing X-ray beams 18A and 18B, respectively). A second subset 40 comprises at least one image data set that does not include dedicated marker 30B (i.e., image data set 34C with image data 36C captured with the probing X-ray beam 18C). In practice, 100 and more image data sets may be taken, so that at least the second subset 40 will typically comprise dozens of data sets.

In the schematic example illustrated in FIG. 3, all three image data sets 34 include the object 12 of interest, i.e., the vertebra 13 shown in FIGS. 2A and 2B. The vertebra 13 is included in all image data sets 34 because it is located in the central volume 24. Since the markers 30 are located in the peripheral volume 26, not all image data sets 34 include all the markers 30. Whereas image data sets 34A and 34B include the dedicated marker 30B, image data set 34C does not includes the dedicated marker 30B. Consequently, image data sets 34A and 34B are assigned to the first subset 38, whereas image data set 34C is assigned to the second subset 40.

In the above example, first and second subsets 38, 40 of image data sets are defined for a dedicated marker 30B. Corresponding subsets may be defined for other markers, such as marker 30C. It will be appreciated that the same image data set may be assigned to the first subset for a dedicated first marker (as it includes the dedicated first marker) and to the second subset for a dedicate second marker (as it does not include the dedicated second marker).

Figure 4A:
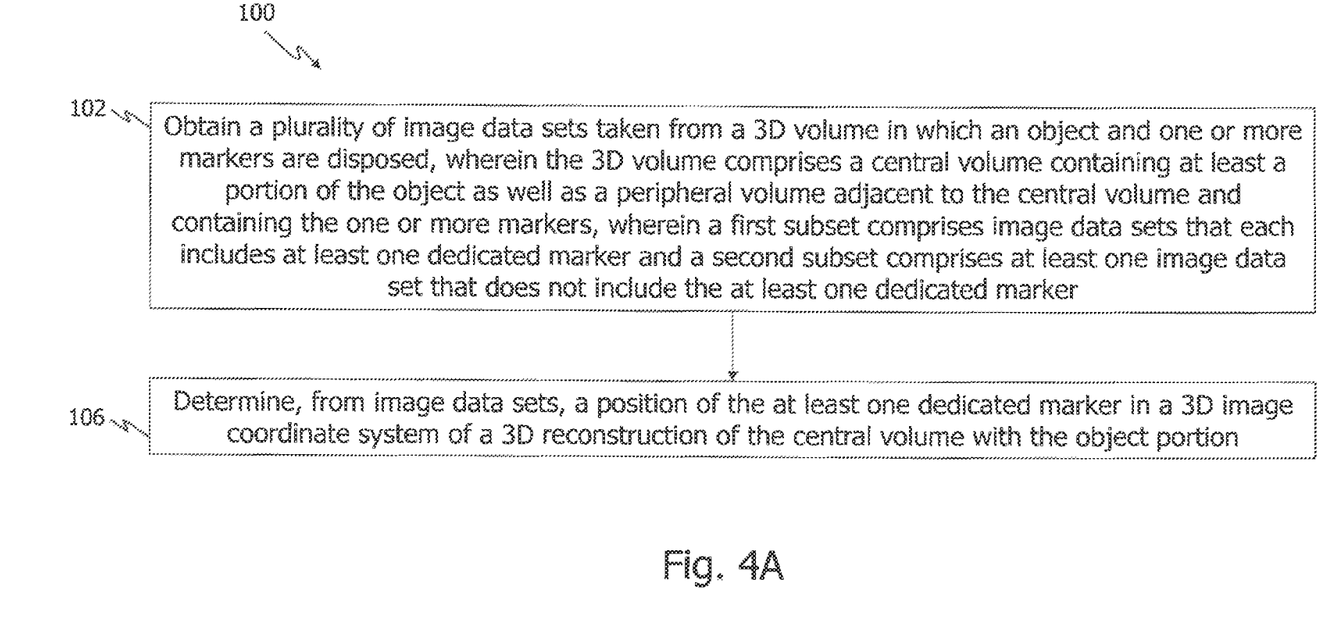
FIG. 4A shows a flow diagram of an embodiment of a method aspect of the present disclosure.
Figure 4B:
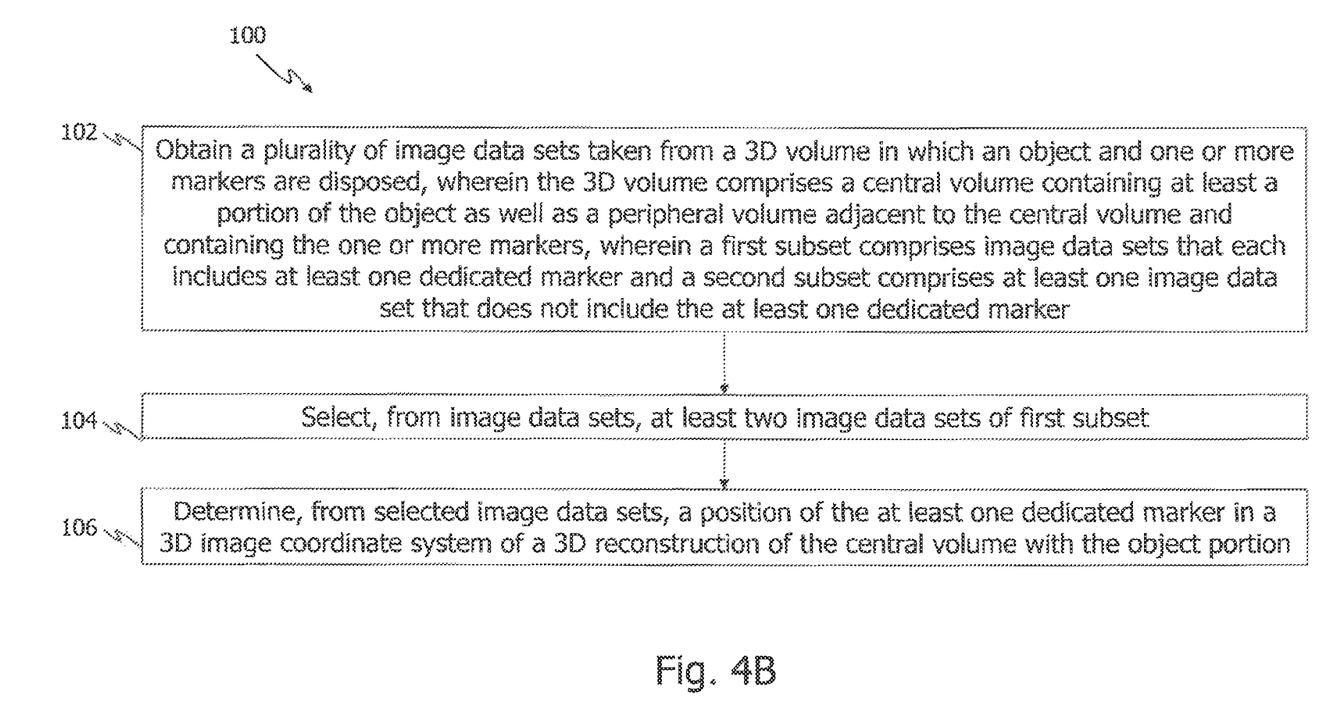
FIG. 4B shows a flow diagram of an embodiment of a variant of the method aspect of the present disclosure.

FIGS. 4A and 4B show a flow diagram of an embodiment of a method aspect of the present disclosure and an optional variant thereof.

Due to the positioning of the markers 30 in the peripheral volume 26, the 3D reconstruction of the central volume 24 does not contain information about the positions of the markers 30 in a 3D image coordinate system of the 3D reconstruction. The information about the marker positions has to be determined from the image data sets as shown in FIGS. 4A and 4B.

Each one of FIGS. 4A and 4B shows a flow diagram 100 of a computer implemented method embodiment of determining the respective position of each of the markers 30 in the 3D coordinate system of the 3D reconstruction of the central volume 24.

The method comprises obtaining in step 102 the plurality of image data sets 34 taken from the 3D volume 20 in which the object 12 (e.g., the vertebrae 13) and the one or more markers 30 are disposed. The image data sets 34 may have been captured using the C-arm 10 of FIGS. 1A and 1C and may be obtained by the computer system via a hardware interface that couples the computer system to the C-arm 10.

As illustrated in FIG. 2A, the 3D volume 20 comprises the central volume 24 containing at least a portion of the object 12 and further comprises the peripheral volume 26 adjacent to the central volume 24 and containing the one or more markers 30. The image data sets 34 have been taken from at least one of different positions and different orientations relative to the object 12 (see FIGS. 1C and 2B for the C-arm example). As illustrated in FIG. 3, a first subset 38 of image data sets 34 comprises image data sets 34A, 34B that each includes the dedicated marker 30B of the one or more markers 30. A second subset 40 of image data sets 34 comprises at least one image data set 34C that does not include the dedicated marker 30B.

The plurality of image data sets 34 may be provided in form of captured image data 36 per image data set 34. Optionally, each of the image data sets 34 comprises additional parameters, such as parameters 37A, 37B, 37C shown in FIG. 3. The additional parameters 37 may include an orientation (e.g., a tilting angle of the C-arm 10) and/or a position of the X-ray sensor 14 for which corresponding image data 36 were captured. The parameters 37 may further include at least one of patient data, time, date, energy and/or wavelength of the emitted and/or detected X-rays, X-ray intensity, type of imaging device, and contrast agent injected into the patient. The image data sets 34 may conform to any standard, such as the DICOM standard Returning to FIG. 4A, the method also comprises determining in step 106, from the image data sets, the position of the at least one dedicated marker in the 3D image coordinate system of the 3D reconstruction of the central volume with the object portion. The step 106 may comprise performing a 3D reconstruction of the central volume 24 and at least a part of the peripheral volume 26 that includes the one or more (e.g., all) markers. Step 106 may also comprise using at least two image data sets of the first subset 38.

Using the different subsets 38, 40 of image data sets 34, the respective positions of one or more of the markers 30 in the 3D image coordinate system may be determined using an approach as illustrated in FIG. 4B. In the computer implemented method embodiment shown in FIG. 4B, the method also comprises selecting in step 104, from the image data sets 34, at least two image data sets 34 of the first subset 38. The selection of the at least two image data sets 34 may comprise a determination of whether an image data set 34 comprises the at least one dedicated marker 30, such as the marker 30B (see 3), and therefore is to be assigned to the first subset 38. This determination may be performed based on automatic image recognition performed for each set of image data 36. The markers 30 may be identified by their shape and/or detected intensity. As explained above, the markers 30 may be artefacts of tracking elements. The trackable device 29 shown in FIG. 2A comprises LEDs connected with electrical circuits via solder joints. These solder joints have comparably low transmittance for X-rays and therefore appear on in a visual representation of the image data 36 as distinguishable dark dots, as indicated for markers 30B and 30C in 3. Therefore, the markers 30 may be identified as artefacts that are constituted by the solder joints for each of the associated LEDs.

The first subset 38 comprises all image data sets 34 that include the dedicated marker 30B. A larger number of image data sets 34 increases the accuracy of the position determination for the dedicated marker 30B. Alternatively, the first subset 38 may comprise only a selection of the image data sets 34 that include the dedicated marker 30B. For example, the first subset 38 may only comprise image data sets 34 that additionally fulfil a quality criterion. Such a quality criterion may define a threshold of number of identifiable markers 30 or a intensity and/or contrast threshold for the markers 30 included in the image data sets 34. A limited number of image data sets 34 also reduces the amount of data that is required to be processed.

The method further comprises determining in step 106, from the selected image data sets 34, a position of the at least one dedicated marker 30B in the 3D image coordinate system of the 3D reconstruction of the central volume 24 with the object 12.

The position of the at least one dedicated marker 30B may be determined according to approaches known in prior art. One example of a method for determining the position is briefly explained below. The example will use two image data sets 34, which is the lowest number of image data sets 34 required to determine the position of the at least one dedicated marker 30B.

In a first step, a position and orientation of the X-ray detector 14 is determined for each of the two image data sets 34 that include the dedicated marker 30B. The position and orientation may be determined from feature recognition inside both images 36, wherein a comparison of the recognized features between both images 36 allows determining the tilting angles of the C-arm under which the two images 36 were taken. Based on a known distance of the X-ray detector 14 relative to the longitudinal axis 22, a position and orientation of the X-ray detector 14 for both images 36 can be determined. Alternatively, the orientation and/or position of the X-ray detector 14 may be provided in form of additional parameters 37 within each image data set 34, as explained above with reference to FIG. 3.

The orientation and/or position are typically given in a 3D image coordinate system in which also the central volume 24 will be reconstructed. This means that the position of the dedicated marker 30B will also be obtained in that 3D image coordinate system of the 3D reconstruction of the central volume 24.

In a second step, two virtual lines, or projections, are determined between the X-ray source 16 and the positions in the sensor area of the X-ray detector 14 at which the dedicated marker 30B was respectively detected.

In a third step, a point of intersection (or smallest distance) of the two virtual lines is determined. The point of intersection is the position of the dedicated marker 30B in the 3D image coordinate system.

The method may also be performed with more than two image data sets 34 containing the at least one dedicated marker 30B. The position of the dedicated marker 30B may then be determined, for example, as an average of a plurality of intersection points or using a least squares method.

The position of the at least one dedicated marker 30B may be determined without determining a position and/or orientation of the X-ray sensor 14 as explained above. A different approach comprises recognizing different features (e.g., features located in the central volume 24) in different image data 36 and determining a distance of the markers 30 relative to recognized features.

Figure 5:
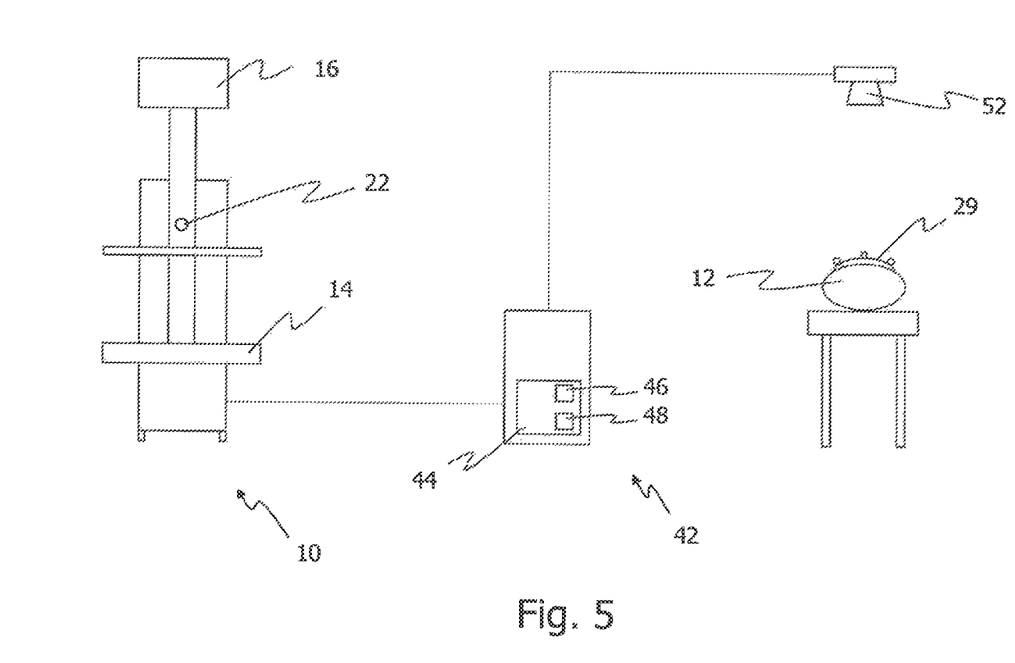
FIG. 5 shows an embodiment of a surgical navigation system realizing a device aspect of the present disclosure.

Once the positions of the marker 30B and of the other markers 30A, 30C have been determined in the 3D image coordinate system, the positions can be processed for surgical navigation purposes. In this regard, FIG. 5 shows an embodiment of a surgical navigation system 42. The surgical navigation system 42 comprises a device 44 for determining a respective position of the markers 30 in the 3D image coordinate system as explained above with reference to FIG. 4B.

In the embodiment shown in FIG. 5, the position determination device 44 comprises a processor 46 and a computer program product 48 comprising program code portions configured to perform the method described above with reference to FIG. 4B when executed by the processor 46. The computer program product 48 may be stored on a computer-readable recording medium, such as a disk drive, compact disk, flash drive, or a server.

The surgical navigation system 42 shown in FIG. 5 further comprises a camera 52 that is configured to detect a trackable device 29. The trackable device 29 may the trackable device 29 shown in FIG. 2A or any other type of tracker described above or known in the art. The surgical navigation system 42 may also use non-optical tracking technologies such as electromagnetic tracking based on tracking elements in the form of coils. As will be appreciated, such coils also create artefacts in the image data sets created by a C-arm or similar imaging device.

A data connection is provided between the position determination device 44 and the C-arm 10 (e.g., the C-arm 10 as described above). The data connection may be a wired connection as shown in FIG. 5. Additionally or alternatively, the data connection may comprise one or both of a wireless connection and an intermediate data storage such as a memory stick, local or remote server for storing data. Over the data connection, the position determination device 44 obtains a plurality of image data sets 34 taken by the C-arm 10 (see, e.g., FIG. 3). The data connection may also be used to send a 3D reconstruction generated from image data sets 34 taken by the C-arm 10 for navigation (e.g., visualisation) purposes to the surgical navigation system 42.

The C-arm 10 or a processor connected to the C-arm 10 generates the 3D reconstruction (in a 3D image coordinate system) based on the plurality of image data sets 34 taken by the C-arm 10. The 3D reconstruction is then sent to the surgical navigation system 42. The 3D reconstruction can consequently be registered with a 3D navigation coordinate system if a sufficient amount of markers 30 can be determined by the position determination device 44 in the 3D image coordinate system and the corresponding tracking elements can be determined by the surgical navigation system 42 in the 3D navigation coordinate system. The sufficient amount of markers 30 may depend on the amount of markers of the trackable device 29 and the amount of degrees of freedoms that the trackable device 29 needs to be tracked in. Typically, the positions of at least three markers 30 need to be determined.

Once the surgical navigation system 42 has access to the determined positions of the three markers 30 (determined by the C-arm 10 or the surgical navigation system 42), the surgical navigation system 42 is configured to register the 3D image coordinate system with a 3D navigation coordinate system. For example, the marker 30B (and the other markers 30A, 30C) is associated with a known position in the 3D navigation coordinate system, for example, based on images captured by the camera 52 of a tracking element (e.g., an LED or reflecting sphere) having a predetermined spatial relationship with the marker 30B (and similar for the markers 30A, 30C). Based on the determined marker positions in the 3D image coordinate system and the associated position in the 3D navigation coordinate system, the 3D image coordinate system and, thus, the 3D reconstruction of the central volume 24 can be registered with the 3D navigation coordinate system. To this end, the surgical navigation system 42 may be configured to determine a transformation that translates the 3D reconstruction inside the 3D navigation coordinate system in such a way that the position of each of the markers in the 3D image coordinate system coincides with the corresponding position associated with each of the markers 30 in the 3D navigation coordinate system. After the registration has been performed, the 3D reconstruction of the central volume 24 can be used for navigation purposes, for example by displaying the position of a surgical instrument tracked by the surgical navigation system 42 relative to the 3D reconstruction including the vertebrae 13 of FIG. 2A.

The above described technique allows processing the 3D reconstruction independently from whether or not markers 30 are located inside the central volume 24. Therefore, the central volume 24 can be defined more freely. In the case of medical imaging this enables limiting the central volume 24 to essential body parts and consequently reduces radiation exposure to the patient.

The features described in relation to the exemplary embodiments shown in the drawings can be readily combined to result in different embodiments. It is apparent, therefore, that the present disclosure may be varied in many ways. Such variations are not to be regarded as a departure from the scope of the invention as defined by the claims appended hereto.

The invention claimed is:

1. A computer-implemented method of determining a respective position of one or more radiopaque markers in a three-dimensional (3D) image coordinate system of a 3D reconstruction of at least a portion of an object of interest for a surgical procedure, the computer-implemented method comprising:

obtaining a plurality of image data sets generated by an imaging device operating on the basis of radiation, the image data sets taken from a 3D volume in which the object and the one or more radiopaque markers are disposed, wherein the 3D volume comprises a central volume containing at least a portion of the object and further comprises a peripheral volume adjacent to the central volume and containing the one or more radiopaque markers such that the central volume does not contain the one or more radiopaque markers, wherein the image data sets have been taken from at least one of different positions and different orientations relative to the object, and wherein the central volume is defined by a largest portion of the 3D volume that is covered by each of the plurality of image data sets;

performing a 3D reconstruction of the central volume based on the image data sets;

defining first and second subsets of the image data sets for at least one dedicated radiopaque marker of the one or more radiopaque markers, wherein the first subset of the image data sets comprises image data sets that each includes the at least one dedicated radiopaque marker and the second subset of the image data sets comprises at least one image data set that does not include the at least one dedicated radiopaque marker; and determining, from the first subset of the image data sets, a position of the at least one dedicated radiopaque marker in a 3D image coordinate system of the 3D reconstruction of the central volume containing the object portion generated from the first and second subsets.

2. The computer-implemented method of claim 1, further comprising:

performing the 3D reconstruction of the central volume without the peripheral volume; and visualizing the 3D reconstruction of the central volume without the peripheral volume.

3. The computer-implemented method of claim 1, wherein the image data sets of the first subset includes a portion of the peripheral volume that contains the at least one dedicated radiopaque marker and is not included in the at least one image data set of the second subset.

4. The computer-implemented method of claim 1, further comprising processing the position of each of radiopaque markers for surgical navigation.

5. The computer-implemented method of claim 4, wherein the at least one dedicated radiopaque marker is associated with a known position in a 3D navigation coordinate system, and wherein processing the position of the at least one dedicated radiopaque marker for surgical navigation comprises registering the 3D reconstruction with the 3D navigation coordinate system by aligning the position of the at least one dedicated radiopaque marker in the 3D image coordinate system with the known position of the at least one dedicated radiopaque marker in the 3D navigation coordinate system.

6. The computer-implemented method of claim 1, wherein the one or more radiopaque markers are one or more artefacts of one or more devices trackable by a surgical navigation system, the one or more artefacts being detectable in the image data sets.

7. The computer-implemented method of claim 6, wherein the one or more trackable devices comprise at least one-light emitting diodes each having a solder joint to comprise one of the one or more artefacts.

8. The computer-implemented method of claim 1, wherein the object portion is an interior portion of the object.

9. The computer-implemented method of claim 1, wherein the one or more radiopaque markers are provided on a registration device, the registration device further including a tracker capable of being tracked by a camera of a navigation system.

10. The computer-implemented method of claim 1, wherein the one or more radiopaque markers are attached to an exterior portion of the object.

11. The computer-implemented method of claim 1, wherein the one or more radiopaque markers comprise two or more radiopaque markers arranged together on a carrier, at least a portion of the carrier being flexible such that a first one of the two or more radiopaque markers on the portion is movable relative to a second one of the two or more radiopaque markers on the portion.

12. The computer-implemented method of claim 6, wherein the one or more trackable devices comprise two or more trackable devices, the one or more radiopaque markers comprise two or more radiopaque markers each having a fixed spatial relationship relative to a light emitting diode of one of the two or more trackable devices, the two or more trackable devices are arranged together on a carrier, and at least a portion of the carrier is flexible such that a first one of the two or more radiopaque markers on the portion is movable relative to a second one of the two or more radiopaque markers on the portion.

13. The computer-implemented method of claim 1, wherein
the central volume has a longitudinal axis and wherein the image data sets have been taken by one of (i) moving an imaging device to different positions about or along the longitudinal axis of the central volume and (ii) moving the object and the one or more radiopaque markers about or along the longitudinal axis.

14. A device for determining a respective position of one or more radiopaque markers in a 3D image coordinate system of a 3D reconstruction of at least a portion of an object of interest for a surgical procedure, the device being configured to:
obtain a plurality of image data sets generated by an imaging device operating on the basis of radiation, the image data sets taken from a 3D volume in which the object and the one or more radiopaque markers are disposed, wherein the 3D volume comprises a central volume containing at least a portion of the object and further comprises a peripheral volume adjacent to the central volume and containing the one or more radiopaque markers such that the central volume does not contain the one or more radiopaque markers, wherein the image data sets have been taken from at least one of different positions and different orientations, and wherein the central volume is defined by a largest portion of the 3D volume that is covered by each of the plurality of image data sets;
perform a 3D reconstruction of the central volume based on the image data sets;
define first and second subsets of the image data sets for at least one dedicated radiopaque marker of the one or more radiopaque markers, wherein the first subset of the image data sets comprises image data sets that each includes the at least one dedicated radiopaque marker and the second subset of the image data sets comprises at least one image data set that does not include the at least one dedicated radiopaque marker; and
determine, from the first subset of the image data sets, a position of the at least one dedicated radiopaque marker in a 3D image coordinate system of the 3D reconstruction of the central volume containing the object portion generated from the first and second subsets.

15. The device of claim 14, wherein the image data sets of the first subset each includes a portion of the peripheral volume that contains the at least one dedicated radiopaque marker and is not included in the at least one image data set of the second subset.

16. A navigation system for tracking an object of interest for a surgical procedure, comprising:
a device configured to:
obtain a plurality of image data sets generated by an imaging device operating on the basis of radiation, the image data sets taken from a 3D volume in which the object and one or more radiopaque markers are disposed, wherein the 3D volume comprises a central volume containing at least a portion of the object and further comprises a peripheral volume adjacent to the central volume and containing the one or more radiopaque markers such that the central volume does not contain the one or more radiopaque markers, wherein the image data sets have been taken from at least one of different positions and different orientations relative to the object, and wherein the central volume is defined by a largest portion of the 3D volume that is covered by each of the plurality of image data sets;
perform a 3D reconstruction of the central volume based on the image data sets;
define first and second subsets of the image data sets for at least one dedicated radiopaque marker of the one or more radiopaque markers, wherein the first subset of the image data sets comprises image data sets that each includes the at least one dedicated radiopaque marker and the second subset of the image data sets comprises at least one image data set that does not include the at least one dedicated radiopaque marker; and
determine, from the first subset of the image data sets, a position of the at least one dedicated radiopaque marker in a 3D image coordinate system of the 3D reconstruction of the central volume containing the object portion generated from the first and second subsets; and
a processing device configured to process the position of the at least one dedicated radiopaque marker for surgical navigation.

17. The computer-implemented method of claim 1, comprising defining the first and second subsets of the image data sets based on a quality criterion such that the image data sets of the first subset each fulfil the quality criterion and the second subset includes at least one of the image data sets that includes the at least one dedicated radiopaque marker and does not fulfil the quality criterion.

18. The computer-implemented method of claim 1, wherein the one or more radiopaque markers comprises a plurality of radiopaque markers, and comprising defining the first and second subsets of the image data sets based on a threshold number of radiopaque markers such that the image data sets of the first subset each includes the at least one dedicated radiopaque marker and a total number of radiopaque markers greater than or equal to the threshold, and the second subset of the image data sets includes at least one image data set that includes the at least one dedicated radiopaque marker and a total number of radiopaque markers less than the threshold.

19. The device of claim 14, wherein the device is configured to define the first and second subsets of the image data sets based on a quality criterion such that the image data sets of the first subset each fulfil the quality criterion and the second subset includes at least one of the image data sets that includes the at least one dedicated radiopaque marker and does not fulfil the quality criterion.

20. The device of claim 14, wherein the one or more radiopaque markers comprises a plurality of radiopaque markers, and the device is configured to define the first and second subsets of the image data sets based on a threshold number of radiopaque markers such that the image data sets of the first subset each contain a total number of radiopaque markers greater than or equal to the threshold, and the second subset of the image data sets includes at least one image data set including the at least one dedicated radiopaque marker and a total number of radiopaque markers less than the threshold.

* * * * *